United States Patent [19]

Chauhan et al.

[11] Patent Number: 5,597,844

[45] Date of Patent: Jan. 28, 1997

[54] CIMETIDINE GRANULES COATED WITH A PARTIALLY HYDROGENATED VEGETABLE OIL

[76] Inventors: Sushil Chauhan; Gordon France; John Buehler, all of SmithKline Beecham Corporation, Corporate Intellectual Property - U.S., UW2220, P.O. Box 1539, King of Prussia, Pa. 19406-0939

[21] Appl. No.: 446,708

[22] PCT Filed: Nov. 22, 1993

[86] PCT No.: PCT/EP93/03272

§ 371 Date: Jul. 14, 1995

§ 102(e) Date: Jul. 14, 1995

[87] PCT Pub. No.: WO94/12180

PCT Pub. Date: Jun. 9, 1994

[30] Foreign Application Priority Data

Nov. 27, 1992 [GB] United Kingdom ............... 9224855

[51] Int. Cl.⁶ .................................................. A61K 31/415
[52] U.S. Cl. ............................................................ 514/400
[58] Field of Search ............................................... 514/400

[56] References Cited

U.S. PATENT DOCUMENTS 5,229,137  7/1993  Wolfe ........................................ 424/687

FOREIGN PATENT DOCUMENTS

| 0290229 | 11/1988 | European Pat. Off. . |
| 0322048 | 6/1989 | European Pat. Off. . |
| WO92/04893 | 4/1992 | WIPO . |
| WO92/21328 | 12/1992 | WIPO . |

*Primary Examiner*—Raymond Henley, III
*Attorney, Agent, or Firm*—Dara L. Dinner; Stephen Venetianer; Edward T. Lentz

[57] ABSTRACT

A non-aqueous, chewable composition for oral delivery of unpalatable drugs is provided. The composition contains the drug intimately dispersed or dissolved in a pharmaceutically acceptable lipid that is solid at room temperatures. The composition also has a matrix that contains a granulating agent for the total composition and a rapid dispersal agent and optionally additives such as buffering agents, flavoring agents, surfactants and the like.

10 Claims, No Drawings

CIMETIDINE GRANULES COATED WITH A PARTIALLY HYDROGENATED VEGETABLE OIL

This application is a 371 of PCT/EP93/03272 filed Nov. 22, 1993.

This invention relates to granules of cimetidine which are useful in the preparation of pharmaceutical compositions having an improved flavour.

Cimetidine is a histamine $H_2$-antagonist and has been described in UK. Patent Specification 1,397,436. Cimetidine has been shown to be useful in the treatment of duodenal, gastric, recurrent and stomal ulceration, and reflux oesophagitis and in the management of patients who are at high risk from haemorrhage of the upper gastrointestinal tract.

Cimetidine is known to have a pronounced bitter taste. This is not usually a problem when the dosage form employed is a capsule or a tablet designed to be swallowed, thereafter to disintegrate upon reaching the stomach. However, such dosage toms can be impractical when it is desired to administer a large amount of active ingredient, or to co-administer a relatively bulky second active ingredient such as an antacid or alginate. Moreover many individuals have difficulty in swallowing a solid dosage form.

A conventional approach to administering relatively large amounts of active ingredient is by means of a suspension or a chewable tablet, i.e. a tablet which disintegrates in the mouth upon being chewed.

It will be appreciated that a major requirement of such dosage forms is that they must be palatable, since an unpalatable formulation increases the risk of a patient neglecting to take a medicament. Such non-compliance with the dosing regimen will in turn delay or prevent the patient's recovery from the condition under treatment.

A further requirement of such compositions is that once the formulation reaches the stomach, the individual particles should release the active ingredient rapidly and completely in order to ensure that substantially all of the active ingredient is absorbed; that is to say the formulation should be bioavailable.

In the case of cimetidine, because of its bitterness, the provision of such dosage forms represents a considerable problem.

EP-A-257823 describes a stable aqueous suspension of cimetidine wherein at least 90% of the cimetidine is in the polymorphic B form. It is disclosed that the use of polymorph B overcomes the problem of polymorphic interconversion found in the case of polymorph A suspensions of relatively low viscosity which tend to result in lumpy and non homogeneous suspensions.

EP-A-322048 describes a pharmaceutical granule composition comprising cimetidine and an ester of a polyhyctroxy compound, in particular a glycerol ester selected from:

a) gylcerol esters having a hydroxyl value of greater than 120;

b) glycerol esters having a hydroxyl value of greater than 60 and having a triglyceride content of less than 30% by weight, and c) gylcerol esters having a hydroxyl value of greater than 5 and a melting point of less than 40° C.

It is disclosed that such cimetidine containing granules are useful in the preparation of chewable tablets.

Coated cimetidine granules have now been discovered which have improved flavour. They can be presented in a variety of pharmaceutical forms, e.g., as a chewable tablet, a constitutable powder, or as a sprinkle powder, i.e., a powder that can be sprinkled, for example, onto food before consumption.

In a first aspect the present invention provides a pharmaceutical composition comprising cimetidine granules coated with a partially hydrogenated vegetable oil or a chemical equivalent thereof, in an amount corresponding to at least 20%, suitably from 25% to 200%, by weight relative to the cimetidine.

More suitably the partially hydrogenated vegetable oil is present in an amount from 50% to 150%, preferably 75% to 125%, particularly 100% by weight relative to the cimetidine.

The cimetidine can exist in any form, for example, polymorph A, B, C or Z or any mixture thereof, preferably polymorph A.

Partially hydrogenated vegetable oils are derived from natural products and generally comprise a mixture of glycerides of $C_{14-20}$ fatty acids, in particular palmitic and stearic acids, said raixmre suitably having an iodine value of less than 10 and a melting point greater than 40° C. Preferably said mixture has an iodine value less than 5 and a melting point between 45° and 75° C.

Suitable examples of partially hydrogenated vegetable oils include partially hydrogenated cottonseed oil, soybean oil, corn oil, peanut oil, palm oil, sunflower seed oil or mixtures thereof. Examples of commercially available oils are those sold by Van Den Burgh Foods Company, USA, and include Stearine 07 (partially hydrogenated cottonseed oil), Stearine 17 (partially hydrogenated soybean oil), Stearine 27 (partially hydrogenated palm oil) and K.L.X. (a mixture of partially hydrogenated cottonseed/soybean oil).

Chemical equivalents of partially hydrogenated vegetable oils include synthetically produced glycerides of $C_{14-20}$ fatty acids having the same properties as the naturally derived products as hereinbefore described.

The coated granules of the present invention can be prepared by adding a partially hydrogenated vegetable oil to cimetidine, warming the mixture until the vegetable oil just melts and mixing for a short period of time until the mixture just granulates. Alternatively, the granules can be prepared in a spray dryer according to conventional techniques. Preferably the granules are prepared in a hot-melt fluid bed coating process for example as described in J Pharmaceutical Research, Vol 7, No. 11, 1990, 1119.

In a second aspect the present invention provides a constitutable powder composition comprising coated cimetidine granules as hereinbefore defined and a suspending agent. Such constitutable powders can be mixed with water in order to prepare extemporaneously aqueous cimetidine suspensions.

It has been found that such aqueous suspensions have the advantage that cimetidine polymorph A can be used in the coated granules of the present invention without suffering from the problem of polymorphic interconversion.

Examples of suspending agents include xanthan gum, hydroxypropylmethylcellulose, methylcellulose, carageenan, sodium carboxymethyl cellulose, and sodium carboxymethyl cellulose/microcrystalline cellulose mixes, particularly sodium carboxymethyl cellulose/microcrystalline cellulose mixtures. Preferred suspending agents are thixotropic suspending agents such as xanthan gum, carageenan and sodium carboxymethyl cellulose/microcrystalline cellulose mixtures and mixtures thereof and particularly preferred suspending agents are Avicel RC591, Avicel RC581 and Avicel CL611. Avicel is a trademark of FMC Corporation, and RC591, RC581 and CL611 are mixtures of microcrystalline cellulose and sodium carboxymethyl cellulose. The mount of suspending agent present will vary according to the particular suspending agent used and the presence or absence of other ingredients which have an ability to act as a suspending agent or which contribute significantly to the viscosity of the composition. In general, however, the mount of suspending agent will lie in the range 1–50% w/w relative to the coated cimetidine granules. When the suspending agent is xanthan gum, it will usually be present in an amount corresponding to 1–20% w/w relative to the coated cimetidine granules whereas when Avicel is used, the amount typically will lie in the range 5–50% w/w, suitably 10–25% w/w. When carageenan or hydroxypropylmethylcellulose is used, typically this will constitute 5–50% w/w relative to the coated cimetidine granules. Suitably, the suspending agent is a mixture of xanthan gum and hyctroxypropylmethylcellulose or Avicel in mounts falling within the ranges noted above.

Suitably, the constitutable powder composition also comprises a suffactant. The surfactant improves the wettability of the coated cimetidine granules. Examples of surfactants include co-block polymers such as poloxamer 188 and partial esters of sorbitan and sorbitol and their polyoxyethylene derivatives, e.g. Tween and Span series of surfactants.

A particularly preferred surfactant is Tween 80 which has been found to minimise the degradation of coated cimetidine granules when in aqueous suspension.

The surfactant is generally present in an amount from 0.1–10%, suitably 1–8%, preferably 2–6%, (w/w) relative to the coated cimetidine granules.

The constitutable powder composition can contain ingredients which improve its taste, for example sweeteners, bitter-taste maskers such as sodium chloride and tastemasking flavours such as contramaxum, flavour enhancers such as monosodium glutamate, and flavouring agents.

Examples of sweeteners include bulk sweeteners such as sucrose, hydrogenated glucose syrup, the sugar alcohols sorbitol and xylitol, and sweetening agents such as sodium cyclamate, sodium saccharin, aspme and ammonium glycyrrhizinate.

A bulk sweetener will usually be present in an amount corresponding to about 50–1000% relative to the coated cimetidine granules, the amount depending in part upon whether other ingredients are present which have a thickening effect on the composition. For example, when sorbitol is used as the sole bulk sweetener and no thickener is present, typically the dry weight of sorbitol present is in the range 200–800% w/w relative to the coated cimetidine granules.

When hydrogenated glucose syrup (solids content approximately 74%) is used as the sole bulk sweetener, typically it is present in an amount 400–1000% w/w relative to the coated cimetidine granules. It will be appreciated that combinations of bulk sweeteners can be used, for example combinations of sorbitol and hydrogenated glucose syrup, or sucrose and sorbitol.

Other excipients which can be used include humectants such as propylene glycol and glycerol and colourants such as titanium dioxide.

Typically the total quantity of humectant present is in the range 0–150% w/w relative to the coated cimetidine granules. Thus, for example, propylene glycol and glycerol can each be present in an amount approximating to 60% w/w.

The constitutable powder composition can contain preservatives to prevent microbial contamination. Examples of preservatives are the alkylparabens, such as methylparaben, propylparaben and butylparaben.

The constitutable powder composition can be prepared by blending the ingredients together to form a dry powder mix which can be packaged into suitable containers for example glass or plastic bottles. Such bottles are sufficiently large so that in use the requisite amount of water can be added whilst leaving sufficient head space to allow efficient shaking of the contents to aid constitution. If desired the coated cimetidine granules can initially be mixed with the surfactant in the presence of sufficient water or glycerol to aid mixing until the surfactant is uniformally adsorbed onto the cimetidine granules. After drying the mixture can be blended with the remaining ingredients.

In a third aspect the present invention provides a chewable tablet comprising coated cimetidine granules as hereinbefore defined.

Such tablets normally contain at least 75 mg of cimetidine. As a maximum the tablet will not normally contain more that 800 mg of cimetidine. Preferably it contains 100 to 200 mg of cimetidine.

The tablets can also contain solid diluents such as sugars and sugar alcohols, for example lactose, xylitol, sorbitol and mannitol. Where desired additional sweeteners can be added, for example ammonium glycyrrhizinate, sodium cyclamate and sodium saccharinate as well as flavours and taste markers, for example sodium chloride and Contramature, and tableting starch, which gives the tablets a palatable texture.

The tablets can also contain other standard tableting excipients for example a disintegrant such as a cross-linked polymeric disintegrant; particular examples being cross-linked polyvinyl pyrrolidone and cross-linked carboxymethyl celluloses.

The compositions of this invention can optionally contain an antacid. An antacid is a pharmaceutically acceptable basic material of sufficient neutralising capacity to neutralise stomach acid. Examples of antacids are aluminium hydroxide, magnesium hydroxide, magnesium carbonate, calcium carbonate, sodium carbonate or bicarbonate and co-dried gels for example aluminium hydroxide-magnesium carbonate co-dried gel. Suitable antacids also include those disclosed in U.S. Pat. No. 5,169,640 and European Patent 294933. Preferably the amount of antacid is such that a unit dose contains 10–30 milliequivalents.

The compositions of this invention can optionally contain an alginate including alginic acid.

The purpose of the alginate is to form a raft of mucilage which floats on the contents of the stomach thereby preventing gastro-oesophageal reflux (GORD) or reducing its symptoms. Usually a carbonate salt such as potassium bicarbonate or sodium bicarbonate is added. Reaction of the carbonate with the acidic gastric juices generates carbon dioxide which aerates the alginate raft, reducing its density and thereby enabling it more easily to float on the stomach contents.

In order to avoid too great an increase in the viscosity in the case of a suspension, a low viscosity grade of alginate is used. Low viscosity grades of alginate suitable for use in the compositions of the present invention will generally have a viscosity of 4–10 mPa.s in 1% aqueous solution at 20° C. Alginates are polymers composed of mannuronic and guluronic acid monomer units. The ratio of mannuronic to guluronic acids determines the raft-forming properties of the alginate and, in general, alginates having a high guluronic-:mannuronic ratio (e.g. 70% guluronic acid) form the strongest rafts. Alginates containing such high levels of guluronic acid are preferably used in the compositions of the present invention, and one such alginate is Protuna/LFR 5/60.

If desired, the present compositions can contain further therapeutic agents, for example, a suitable chewable tablet comprises coated cimetidme granules as herein defined, an antacid, an alginate and simethicone.

The preferred size for the coated cimetidine granules is dependent upon their use. For sprinkle powders and constitutable powders, generally the coated granules have an apparent diameter of less than 250 μm, preferably less than 180 μm. For chewable tablets the granules preferably pass through a 1 mm sieve but are retained by a 0.2 mm sieve.

The present invention is illustrated by the following Examples.

EXAMPLE 1

Cimetidine-partially hydrogenated cotton seed oil granules.

Granules containing cimetidine (50%) and partially hydrogenated cotton seed off (stearine 07) (50%) (w/w) are prepared by spraying molten coating material onto a fluidised bed of cimetidine granules.

EXAMPLE 2

Cimetidine-partially hydrogenated soybean oil granules.

In a similar manner to Example 1 granules are obtained containing cimetidine (50%), and partially hydrogenated soybean oil (stearine 17) (50%) (w/w).

EXAMPLE 3

Cimefidine Consfitutable Powder

| Ingredients | % w/w dry powder mix | g per 100 ml after constitution |
|---|---|---|
| Coated cimetidine granules (Ex. 1) | 19.56 | 8.0 |
| Xanthan Gum | 0.98 | 0.4 |
| Hydroxypropylmethylcellulose | 7.82 | 3.2 |
| Tween 80 | 0.98 | 0.4 |
| Aspartame | 0.98 | 0.4 |
| Colloidal Silicon Dioxide | 1.22 | 0.5 |
| Sorbitol | 61.12 | 25.0 |
| Sodium Carbonate | 3.67 | 1.5 |
| Flavours | 3.67 | 1.5 |
| Total | 100.00 | 40.9 |

The coated cimetidine granules are blended with the remaining ingredients to form a constimtable dry powder mix which is packed into glass or plastic bottles each to contain 81 g of dry powder mix. Each bottle is sufficiently large so that in use the requisite amount of water can be added to the container to produce a final volume of 200 ml, whilst leaving sufficient head space in the bottle to allow efficient shaking of the contents to aid constitution. When constituted the suspension contains 200 mg cimetidine per 5 ml.

EXAMPLE 4

Cimetidine 100 mg Chewable Tablet

| Ingredients | mg/tablet |
|---|---|
| Coated Cimetidine Granules (Example 1) | 200.0 |
| Direct Compression Grade Sorbitol | 790.0 |
| Direct Compression Grade Lactoses: | |
| Crystalline | 500.0 |
| Spray dried | 500.0 |
| Croscarmellose Sodium Type A | 60.0 |
| Sodium Saccharin (Dried Fine Powder) | 2.0 |
| Aspartame | 2.0 |
| Flavourings | 16.0 |
| Magnesium Stearate | 45.0 |
| Total | 2,115.0 |

The coated cimetidine granules are blended with the remaining ingredients and the resulting mixture is compressed to form tablets.

EXAMPLE 5

Cimetidine 200 mg Chewable Tablet

| Ingredients | mg/tablet |
|---|---|
| Coated Cimetidine Granules (Example 1) | 400.0 |
| Direct Compression Grade Sorbitol | 790.0 |
| Direct Compression Grade Lactoses: | |
| Crystalline | 450.0 |
| Spray dried | 450.0 |
| Croscarmellose Sodium Type A | 60.0 |
| Sodium Saccharin (Dried Fine Powder) | 10.0 |
| Aspartame | 1.0 |
| Flavourings | 17.5 |
| Magnesium Stearate | 45.0 |
| Total | 2,223.5 |

The coated cimetidine granules are blended with the remaining ingredients and the resulting mixture is compressed to form tablets.

EXAMPLE 6

Cimetidine 200 mg/Aiginate Chewable Tablet

| Ingredients | mg/tablet |
|---|---|
| Coated Cimetidine Granules (Example 2) | 400 |
| Alginic acid | 500 |
| Sodium Bicarbonate | 170 |
| Sorbitol | 680 |
| Pregelatinised Starch | 30 |
| Croscarmellose Sodium Type A | 60 |
| Lactose | 330 |
| Aspartame | 5 |
| Sodium Saccharin | 5 |
| Magnesium Stearate | 35 |
| Flavours | 50 |
| Total | 2265 |

The coated cimetidine granules are blended with the remaining ingredients and the resulting mixture is compressed to form tablets.

EXAMPLE 7

Cimetidine 200 mg/Alginate/Antacid/Simethicone Chewable Tablet

| Ingredients | mg/tablet |
|---|---|
| Coated Cimetidine Granules (Example 1) | 400 |
| Aluminium Hydroxide Dried Gel | 225 |
| Magnesium Hydroxide | 175 |
| Alginic Acid | 300 |
| Simethicone | 30 |
| Sorbitol (Direct Compression Grade) | 900 |

-continued

| Ingredients | mg/tablet |
| --- | --- |
| Lactose (Direct Compression Grade) | 300 |
| Pregelatinised Starch | 30 |
| Croscarmellose Sodium Type A | 60 |
| Aspartame | 5 |
| Sodium Saccharin | 5 |
| Flavours | 40 |
| Magnesium Stearate | 30 |
| Total | 2500 |

The coated cimetidine granules are blended with the remaining ingredients and the resulting mixture is compressed to form tablets.

We claim:

1. A pharmaceutical composition comprising cimetidine granules coated with a partially hydrogenated vegetable oil or a chemical equivalent thereof, in an amount corresponding to at least 20% by weight relative to the cimetidine.

2. A composition according to claim 1 wherein the partially hydrogenated vegetable oil is present in an amount from 50% to 150% by weight relative to the cimetidine.

3. A composition according to claim 1 wherein the oil is partially hydrogenated cotton seed oil or partially hydrogenated soybean oil or a mixture thereof.

4. A pharmaceutical constitutable powder composition comprising coated cimetidine granules according to claim 1 and a suspending agent.

5. A composition according to claim 4 further comprising a surfactant.

6. A composition according to claim 5 wherein the surfactant is Tween 80.

7. A chewable tablet comprising coated cimetidine granules according to claim 1.

8. A pharmaceutical composition according to claim 1 further comprising an antacid.

9. A pharmaceutical composition according to claim 1 further comprising an alginate.

10. A pharmaceutical composition according to claim 1 further comprising simethicone.

* * * * *